(12) United States Patent
McMinn

(10) Patent No.: US 8,926,707 B2
(45) Date of Patent: Jan. 6, 2015

(54) FEMORAL IMPLANT

(76) Inventor: Derek James Wallace McMinn, Westmidlands (GB)

( * ) Notice: Subject to any disclaimer, the term of this patent is extended or adjusted under 35 U.S.C. 154(b) by 0 days.

(21) Appl. No.: 13/641,990

(22) PCT Filed: Apr. 19, 2011

(86) PCT No.: PCT/GB2011/000595
§ 371 (c)(1),
(2), (4) Date: Nov. 16, 2012

(87) PCT Pub. No.: WO2011/131927
PCT Pub. Date: Oct. 27, 2011

(65) Prior Publication Data
US 2013/0060347 A1 Mar. 7, 2013

(30) Foreign Application Priority Data

Apr. 19, 2010 (GB) .................................. 1006527.4

(51) Int. Cl.
*A61F 2/36* (2006.01)
*A61F 2/30* (2006.01)

(52) U.S. Cl.
CPC ............. *A61F 2/3603* (2013.01); *A61F 2/3662* (2013.01); *A61F 2/3676* (2013.01); *A61F 2/3094* (2013.01); *A61F 2002/30112* (2013.01); *A61F 2002/30332* (2013.01); *A61F 2002/30451* (2013.01); *A61F 2002/3092* (2013.01); *A61F 2002/3619* (2013.01); *A61F 2002/3686* (2013.01); *A61F 2002/369* (2013.01); *A61F 2310/00023* (2013.01); *A61F 2310/00029* (2013.01); *A61F 2310/00179* (2013.01)
USPC .................. 623/23.14; 623/23.23; 623/23.24; 623/23.44

(58) Field of Classification Search
CPC A61F 2002/369; A61F 2/3662; A61F 2/3676
USPC ............ 623/22.4, 22.42, 23.15, 23.23, 23.24, 623/23.29–23.31, 23.44
See application file for complete search history.

(56) References Cited

U.S. PATENT DOCUMENTS 2,679,245 A 5/1954 Timmermans
4,846,839 A 7/1989 Noiles
(Continued)

FOREIGN PATENT DOCUMENTS

DE 4441178 A1 5/1996
DE 102008017014 A1 10/2009
(Continued)

OTHER PUBLICATIONS

GB Search Report dated Auguat 17, 2010 for corresponding GB Patent Application No. 1006527.4.
(Continued)

*Primary Examiner* — David H Willse
*Assistant Examiner* — Javier Blanco
(74) *Attorney, Agent, or Firm* — Morgan, Lewis & Bockius LLP

(57) ABSTRACT

A femoral implant (10) comprises a distal end and a proximal end. A stem (12) is provided at the distal end of the implant (10) and comprises a rounded tip (16) for insertion into a femur, in use, and a body (18) of generally tapering form extending in a distal direction from a base to the tip (16). A femoral head (14) is provided at the proximal end of the implant (10) and extends from the base (20) of the stem (12). The body (18) of the stem (12) includes a plurality of discrete steps (22, 24, 26, 28, 30), located between the tip (16) and the base (20), and the steps (22, 24, 26, 28, 30) are concentrated more towards the base (20) of the stem (12) than towards the tip (16).

11 Claims, 4 Drawing Sheets

(56) References Cited

U.S. PATENT DOCUMENTS

| | | | | |
|---|---|---|---|---|
| 5,702,479 | A | * 12/1997 | Schawalder | ............... 623/23.15 |
| 5,755,789 | A | 5/1998 | Deckner | |
| 5,755,805 | A | 5/1998 | Whiteside | |
| 2003/0187514 | A1 | 10/2003 | McMinn | |
| 2007/0118229 | A1 | * 5/2007 | Bergin et al. | ............. 623/23.31 |
| 2009/0043397 | A1 | 2/2009 | Park | |

FOREIGN PATENT DOCUMENTS

| | | | |
|---|---|---|---|
| EP | 0093869 | A1 | 11/1983 |
| EP | 0684023 | A1 | 11/1995 |
| EP | 0709071 | A2 | 5/1996 |
| EP | 0780106 | A2 | 6/1997 |
| EP | 1344505 | A2 | 9/2003 |
| EP | 1407728 | A1 | 4/2004 |
| EP | 1570811 | A1 | 9/2005 |
| GB | 2028137 | A | 3/1980 |
| WO | WO-2009071940 | A1 | 6/2009 |

OTHER PUBLICATIONS

International Search Report for International Application No. PCT/GB2011/000595, issued Jul. 15, 2011 and mailed Jul. 27, 2011.
Office Action for Chinese Patent Application No. 201180030188.9 mailed Jul. 23, 2014 and English language summary (11 pages).

* cited by examiner

FEMORAL IMPLANT

CROSS-REFERENCE TO RELATED APPLICATIONS

This application is a U.S. National Phase Application of PCT/GB2011/000595, filed Apr. 19, 2011, which claims priority to and the benefit of United Kingdom Patent Application No. 1006527.4, filed Apr. 19, 2010. The entire disclosure of each of these applications is incorporated by reference herein.

FIELD OF THE INVENTION

The present invention relates to a femoral implant. Particularly, but not exclusively, the invention relates to a femoral implant used to resurface a partially resected femoral head.

BACKGROUND TO THE INVENTION

Traditional total hip replacements involve inserting a stem of a femoral implant into the medullary canal of a patient's femur after the femur has been resected at the distal end of the femoral neck. The stem is usually tapered such that its sides gradually converge from a wider proximal end to a narrower distal end. This configuration allows the stem to fill the majority of the medullary canal as the femur gradually narrows in a distal direction and this helps to anchor the implant in the femur. A rounded tip is provided at the distal end of the stem and a femoral neck and head is provided at the proximal end. The femoral head is constituted by a spherical ball configured for location within a corresponding acetabular cup.

In recent years, more conservative approaches, such as hip resurfacing, have been employed rather than total hip replacement as described above. In this case the aim is to save as much healthy bone as possible and so the femur is preferably resected towards the proximal end of the femoral neck or even through the lower portion of the femoral head. The femoral head of the implant in the later case comprises a part-spherical exterior surface (configured for location within a corresponding acetabular cup) and an interior surface shaped to locate the femoral head on the remaining resected bone of the femur. This generally requires that the stem is relatively narrow at its proximal end so that there is room for sufficient healthy bone to be received within the profile of the femoral head to secure it in place. However, this configuration does not allow the stem to fill the majority of the medullary canal to anchor the implant in the femur.

Granted UK patent number GB2388321 discloses an improved stem profile conceived by the present inventor, which is suitable for use in hip resurfacing surgery, and which aims to address the above-mentioned problem. This stem profile has, at a proximal end thereof, a section having an external surface of frustoconical or generally frustoconical form. A base portion is provided at the maximum diameter of the section, which extends substantially axially away from, and is substantially the same diameter as, the end of the resected head into which the stem is to be inserted, in use. Whilst the shape of this stem is advantageous in transferring longitudinal loads through the femur after bone in-growth into the porous coating of the frustoconical section has occurred (usually a few weeks after surgery), loading before the bone has grown into the porous area has been found to be troublesome. More specifically, it has been observed that if patients ignore instructions to use crutches for two months immediately following surgery in order to lessen the load through the hip joint, the frustoconical section may act like a log splitter and break open the base of the femoral head and femoral neck. In such a case, revision surgery using conventional total hip replacement techniques, as described above, may be required.

The present inventor has devised an improvement to the stem profile disclosed in GB2388321 in order to try to stop the stem from being rammed into the base of the femoral head if the patient takes too much load before bone in-growth has occurred. This improvement consists of a flange extending circumferentially around the base of the frustoconical section to abut the periphery of the resected femur. However, the use of partial weight-bearing crutches for the first two months after surgery is still insisted upon as a precaution.

To add to the above, it has been found that the thick stem of the implant disclosed in GB2388321 can touch or come close to the bone of the femoral neck cortex, particularly on the inner (medial) side. This causes the bone in this contact region to preferentially lock onto the stem such that loads are passed down through the stem, bypassing the proximal bone in the femoral head and upper part of the femoral neck, and transferring to the contact region further down the femoral neck. Since bone responds to loads placed upon it and wastes away if it is not normally loaded, the bone in the base of the femoral head and upper part of the femoral neck will become thin and weak in this instance. This phenomenon is commonly known as stress shielding and is clearly an undesirable effect.

A further problem commonly encountered is that the bone into which the stem is inserted is not homogenous. This is particularly the case when dealing with arthritic patients. Usually the bone on one side of the femur is more dense than the bone on the opposite side, which is much softer. This has the effect that, when the stem of the implant is being inserted using a typical interference or press-fit technique, the denser bone does not compress as much as the softer bone and the path of insertion of the implant alters such that the implant moves away from the denser bone towards the softer bone. This results in a skew insertion (mis)alignment whereby the proximal end of the stem does not sit as intended within the recess prepared for it. This leads to stress concentration in the adjacent bone with a risk of fracture or implant loosening.

It is therefore an aim of the present invention to provide an improved femoral implant.

SUMMARY OF THE INVENTION

According to a first aspect of the present invention there is provided a femoral implant comprising a distal end and a proximal end; a stem is provided at the distal end of the implant; the stem comprises a rounded tip for insertion into a femur, in use, and a body of generally tapering form extending in a distal direction from a base to said tip; a femoral head is provided at the proximal end of the implant and extends from the base of the stem; and wherein the body of the stem includes a plurality of discrete steps located between said tip and said base, wherein the steps are concentrated more towards the base of the stem than towards the tip.

Embodiments of the present invention therefore provide a femoral implant which is configured to better distribute loads applied substantially along the stem axis to the adjacent cancellous bone, when in use. Loads will be transferred through distal surfaces of each step. The higher concentration of steps towards the base of the stem will have the effect of more loads being distributed to the cancellous bone around the base than to the cancellous bone deeper inside the femur. This will reduce the risk of the stem being forced further into the femur than intended, either when the implant is inserted during surgery or when high loads are experienced before bone in-growth has occurred to lock the implant in position. Thus, the steps of the present invention provide a series of stops to prevent distal migration of the implant. The present configuration also reduces the risk of stress shielding since it helps to more evenly distribute loads to the cancellous bone surrounding the stem as opposed to channeling the loads along the stem to a more focused area or to the harder cortical bone at the outer regions of the femur. Furthermore, the steps of the present invention can help to ensure that the stem is inserted in the desired position and not misaligned within the femur as a result of encountering different bone densities in the path of insertion. More specifically, the increasing concentration of the steps will induce a self-righting or self-centering action on the alignment of the stem during insertion of the stem into a femur.

It will be understood that the steps will provide a higher degree of resistance (to substantial movement of the stem in a distal direction) between the stem and the femur in the region adjacent the base than in the region adjacent the tip.

The steps may be distributed along the body such that the distance between each adjacent step decreases towards the base. Thus, the steps may become gradually more concentrated towards the base of the stem. The number of steps provided may vary depending on the length and/or width of the stem. In certain embodiments, 3 to 10 steps may be provided.

Some or all of the steps may be located towards the base of the stem. This will serve to further increase the resistance between the stem and the surrounding bone in the region of the base and thereby reduce the risk of the stem being forced further into the femur than desired when high loads are experienced at the base before bone in-growth has occurred.

The width of the steps may increase towards the base. This will also serve to increase the resistance to movement of the stem after fitting to a femur. The steps may have a width of no less than 2 mm so as to provide an adequate surface area for the transfer of load to the femur. In some embodiment, the steps may have a minimum width of approximately 2 mm. The steps may increase in width (by, for example, intervals of 1 mm or 2 mm) up to a maximum of approximately 10 mm. It will be understood that larger step sizes may be required in larger stems. For example, a small stem may have a width of 32 mm at its base and a large stem may have a width of 58 mm at its base.

One of more of the steps may be configured to for a press-fit engagement into the prepared bone of the femur. Where a plurality of the steps are configured for a press-fit engagement, each of said steps may be configured such that the force required for each press-fit engagement decreases towards the base of the stem. Alternatively or additionally, one or more of the steps may be configured for a line-to-line fit engagement into the prepared bone of the femur.

In a particular embodiment, the steps will be configured such that at least the most distal step will have a press-fit engagement and at least the most proximal step will have a line-to-line fit engagement.

In one embodiment, one or more of the steps may include a planar distal stop surface extending substantially radially outwardly from the longitudinal axis of the stem. Each of said steps may also include a substantially cylindrical side surface extending generally parallel to the longitudinal axis of the stem. Thus, one or more of the steps may be of a substantially cylindrical form.

In other embodiments, one or more of the steps may include sloped, curved or irregular-shaped distal stop surfaces and/or sloped, curved or irregular-shaped side surfaces.

The most distal step may be provided approximately halfway between the tip and the base.

Between the tip and the most distal step, the stem may be of a width no greater than one fifth of the width of the base. It will be understood that employing a thin stem at the distal end of the implant will greatly reduce the risk of the stem touching or coming close to the inner aspect of the cortical bone of the femoral neck, thus further reducing the risk of stress shielding.

In another embodiment, the stem may be of a width no greater than one quarter of the width of the base between the tip and the most distal step. In still other embodiments, the stem may be of a width no greater than one third of the width of the base between the tip and the most distal step.

In certain embodiments, the stem may have a width of from approximately 5 mm to 12 mm (e.g. 6 mm, 8 mm or 10 mm) between the tip and the most distal step.

The surface of the stem from the tip to the most distal step may be non-porous to minimise the risk of bone locking onto this region and causing stress shielding. Furthermore, the surface of the stem from the tip to the most distal step may be polished to further minimise the risk of bone locking onto this region and causing stress shielding.

One or more portions of the stem may be configured to be cemented to the femur, in use, or they may be configured such that bone in-growth will fix the stem in place. Thus, one or more portions of the stem may comprise a porous surface. The porous surface may be provided by a porous coating, for example, by providing (cast or sintered) beads or bead portions on the surface or by plasma spraying material such as titanium onto the surface. In some embodiments, the porous surface may be constituted by a porous lattice (for example, as described in the Applicant's co-pending UK patent application numbers GB0922339.7 and GB1000744.1). In a particular embodiment, the portion of the stem from the most distal step to the base will be provided with a porous surface so as to permit bone to lock onto this region. It will also be understood that the porous surface of the stem may help to prevent rotation of the implant due to an increase in frictional resistance between the implant and the bone, particularly when a press-fit engagement is employed.

The stem may be substantially straight or curved.

The base of the stem may be of substantially the same diameter as the proximal end of the prepared femur into which the stem is inserted, in use.

The femoral head of the implant may comprise a part-spherical external surface configured to be received within a corresponding acetabular cup. A free periphery of the part-spherical surface may form an annular skirt extending around the base of the stem. Thus, an internal channel may be provided between the annular skirt and the proximal region of the stem. The internal channel may be configured for a press-fit (appositional) engagement with the proximal end of a prepared femoral head. This arrangement serves to prevent the prepared femoral head from bursting or splitting if the patient fully loads the hip joint before bone in-growth into the implant has occurred.

In one embodiment, the internal channel may be substantially surrounded by a porous surface such as those described above. Thus, the inner surface of the annular skirt may comprise a porous surface as well as the proximal region of the stem.

The femoral head of the implant may comprise a central portion which is substantially hollow. This is advantageous in reducing the weight of the femoral implant, particularly when the implant is formed substantially of metal.

The formation of the hollow portion may be achieved by casting a first part comprising the stem with a radial flange provided at the base of the stem and an annular skirt of the femoral head depending in a distal direction from the outer circumference of the flange, and a second part comprising a part-spherical external surface of the femoral head, at least one of the first or second parts having a cavity therein; and welding the first and second parts together such that the external surface of the femoral head extends in a proximal direction from the outer circumference of the flange. The step of welding the first and second parts together may comprise e-beam welding.

Alternatively, the formation of the hollow portion may be achieved by forming a hollow internal component (for example, by welding together two parts, at least one of which has a cavity therein) of a material having a higher melting point than the remainder of the implant and which includes at least one leg which is incorporated into a mould for the implant; the remainder of the implant being cast and then removed from the mould; and the projecting portion of the leg then being removed so that the implant has the desired external structure.

The projecting portion of the leg may be cut and filed such that is made flush with the surrounding surface of the implant.

Two, three, four or more legs may be provided to position the internal component within the mould. The legs may be evenly disposed around the internal structure. The leg(s) may be configured to project through a flange of the implant which connects the stem to the annular skirt.

The internal component may comprise a titanium alloy. The remainder of the implant may comprise cobalt chrome. The mould may be formed from a ceramic slurry.

The femoral head of the implant may be integral with the stem or may be separable therefrom. Where the femoral head is separable from the stem, both the femoral head and the stem may comprise respective interfitting parts. In one embodiment, a frustoconical spigot may extend from the proximal end of the base of the stem to be received in a complementary shaped cavity in the internal portion of the femoral head, prior to insertion of the implant into a patient. The spigot may be configured for a tight frictional fit in the cavity (for example, by including a so-called Morse taper) and/or may be cemented therein.

The femoral implant may be formed of material comprising cobalt chrome or any other bio-acceptable material such as titanium, stainless steel or ceramic.

According to a second aspect of the present invention there is provided a stem for a femoral implant comprising a rounded tip for insertion into a femur, in use, and a body of generally tapering form extending in a distal direction from a base to said tip; and wherein the body of the stem includes a plurality of discrete steps located between said tip and said base, wherein the steps are concentrated more towards the base of the stem than towards the tip.

According to a third aspect of the present invention there is provided a hip joint prosthesis comprising a femoral implant according to the first aspect of the present invention and an acetabular cup configured to receive the femoral head of said femoral implant.

According to a fourth aspect of the present invention there is provided a method of inserting a femoral implant into a femur comprising:
  resecting the head of the femur;
  preparing a cavity in the femur for receipt of a stem of the implant;
  inserting the stem of the implant into the cavity; and
  impacting the head of the implant onto the resected head of the femur;
  wherein the step of preparing the femur comprises forming a plurality of discrete ledges in the cavity wall for mating with a corresponding plurality of steps provided on the stem of the implant.

The femoral implant may be in accordance with the first aspect of the present invention.

In specific embodiments, the ledges are formed in the (soft) cancellous bone of the femur by a reamer. The reamer may comprise a size-specific rotary mill which may be driven by power and may comprise a guide to produce precise cuts in the cancellous bone for accurate fitting of the stem. It will be understood that, by forming ledges in the cancellous bone, the steps of the stem are not permitted to make contact with (or come close to) the cortical bone around the periphery of the femur. This is advantageous because it reduces the risk of stress-shielding. On the contrary, it is noted that certain prior art prosthesis include small jagged edges which are designed to crush the cancellous bone and to take purchase on the hard cortical bone.

The step of resecting the head of the femur may comprise shaping the outer periphery of the resected head for press-fit engagement with a skirt of the head of the implant. The outer periphery of the resected head may be shaped such that the majority of the skirt is contact with cancellous bone of the femoral head, although the free end of the skirt may abut a small area of cortical bone.

It is noted that certain prior art devices are deliberately designed so that the skirt of the femoral head does not mate completely with the resected end of the femur. Instead, the stem of such devices is inserted in a first procedure and then the head is impacted on the stem to leave a clear gap between the head skirt and the prepared bone of the head so as to prevent any damage resulting during engagement of the head on the stem (e.g. to stop any fouling of a tapering engagement mechanism).

In relation to the present invention, the head and the stem of the implant may either be formed in one piece or the head may be fitted to the stem before the implant is impacted onto the femur. Accordingly, the head of the implant can comprise a skirt configured for press-fit engagement onto the resected femoral head to provide an anti-bursting (i.e. containment) effect, without the risk of damage being caused to the interface between the head and stem of the implant.

The optional features described above in relation to the first aspect of the present invention may also be applied to the second and third aspects of the invention, where applicable.

BRIEF DESCRIPTION OF THE DRAWINGS

Specific embodiments of the present invention are described in more detail below with reference to the accompanying drawings, in which.

DETAILED DESCRIPTION OF CERTAIN EMBODIMENTS

Figure 1:
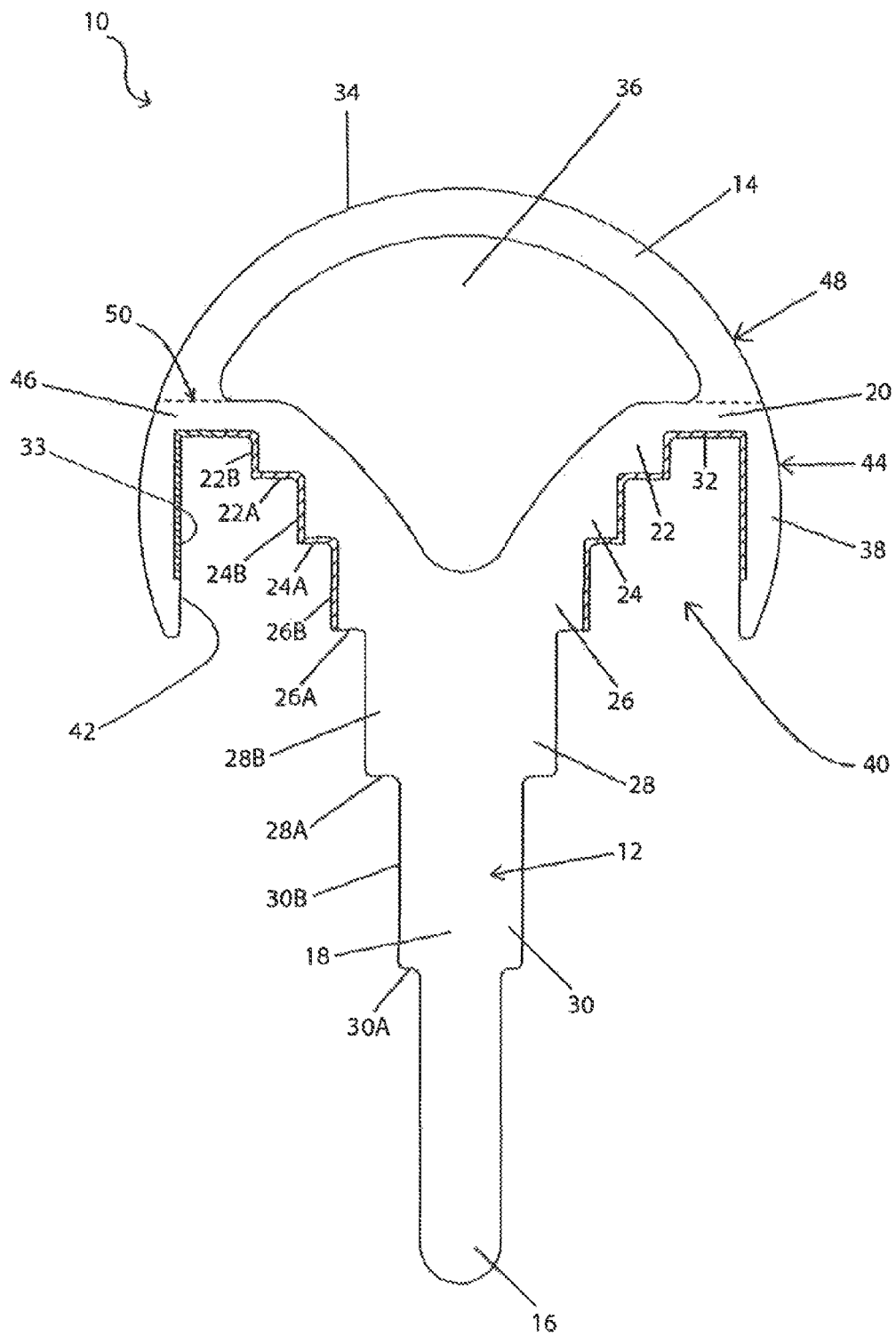
FIG. 1 shows a central cross-sectional view through a femoral implant according to a first embodiment of the present invention, wherein the femoral stem is integral with the femoral head.

With reference to FIG. 1, there is illustrated a femoral implant 10 according to a first embodiment of the present invention. The femoral implant 10 comprises stem 12 and a femoral head 14. The stem 12 is provided at the distal end of the femoral implant 10, when in use. The stem 12 includes a rounded tip 16 configured for insertion into a prepared femur, in use. The stem 12 also includes a body 18 of generally tapering form extending in a distal direction from a base 20 which is locatable, in use, at a proximal end of the prepared femur, to the tip 16. The body 18 in the present embodiment includes five discrete steps 22, 24, 26, 28, 30 located between the base 20 and the tip 16 although the steps 22, 24, 26, 28, 30 are more concentrated towards the base 20.

More specifically, the steps 22, 24, 26, 28, 30 are arranged such that the most distal step 30 is located at approximately 60% of the distance from the base 20 to the tip 16, the next most distal step 28 is located at approximately 40% of the distance from the base 20 to the tip 16, the next most distal step 26 is located at approximately 20% of the distance from the base 20 to the tip 16, the next most distal step 24 is located at approximately 12% of the distance from the base 20 to the tip 16, and the last most proximal step 22 is located at approximately 5% of the distance from the base 20 to the tip 16. Thus, the steps 22, 24, 26, 28, 30 are distributed along the body 18 such that the distance between each adjacent step 22, 24, 26, 28, 30 decreases towards the base 20.

In this particular embodiment each step 22, 24, 26, 28, 30 is generally cylindrical having a planar stop surface 22A, 24A, 26A, 28A, 30A extending substantially radially outwardly from the longitudinal axis of the stem 12 and a substantially cylindrical side surface 22B, 24B, 36B, 28B, 30B extending generally parallel to the longitudinal axis of the stem 12.

The width of the most distal step 30 is less than that of the three next most distal steps 28, 26, 24 and the width of each of those steps is less than that of the most proximal step 22. Furthermore, the base 20 extends outwardly around the most proximal step 22 to form a further planar stop surface 32 which is of substantially the same diameter as, and is configured to mate with, the proximal end of the prepared femur, in use. The width of the stop surface 32 is greater than the width of the most proximal step 22.

In the present embodiment, the two most distal steps 30, 28 are configured for a press-fit engagement into the prepared bone of the femur. However, the force required for the press-fit of the most distal step 30 is greater than that for the next most distal step 28. The next steps 26, 24, 22 are configured for line-to-line fit engagement into the prepared bone of the femur.

The above-described configuration for the steps 22, 24, 26, 28, 30 ensures that substantial movement of the stem 12 in a distal direction, after location within a femur, is minimised. This is because the planar stop surfaces 22A, 24A, 26A, 28A, 30A and 32 serve to transfer loads applied to the base 20 of the stem 12 to the surrounding bone rather than simply channelling these forces through the stem 12 to the tip 16 causing the stem to embed deeper into the bone than intended. Furthermore, the steps 22, 24, 26, 28, 30 serve to induce a self-righting action on the alignment of the stem 12 during insertion into the femur since the angular nature of the steps acts as a guide during insertion.

Between the tip 16 and the most distal step 30, the stem 12 is of a width approximately equal to 14% of the width of the base 20. Employing such a thin stem 12 at the distal end is believed to greatly reduce the risk of the stem 12 touching or coming close to the inner aspect of the cortical bone of the femoral neck, thus reducing the risk of stress shielding. In addition, the surface of the stem 12 from the tip 16 to the third most distal planar stop surface 26A is non-porous and polished to further minimise the risk of bone locking onto this region and causing stress shielding. However, the surface of the stem 12 from the third most distal cylindrical side surface 26B to the base 20 is porous so as to permit bone to lock onto this region. This is advantageous because bone in-growth in this region will help to secure the stem 12 in place and reduce the risk of distal migration of the femoral implant 10 when high loads are experienced. In the embodiment of FIG. 1, the porous surface is provided by a porous lattice 33.

In the embodiment shown in FIG. 1, the stem 12 is substantially straight. However, in other embodiments the stem 12 may curve in the direction of the medullary canal of the femur into which it is being placed.

The femoral head 14 is provided at the proximal end of the femoral implant 10 and extends from, and is integrally welded to, the base 20 of the stem 12. The femoral head 14 includes a part-spherical external surface 34 which is configured to be received within a complementary internal surface of an acetabular cup (not shown). In the present embodiment, the central portion 36 of the femoral head 14 is hollow.

A free periphery of the part-spherical surface 34 forms an annular skirt 38 extending around the base 20 of the stem 12. Thus, an internal channel 40 is provided between the annular skirt 38 and the proximal region of the stem 12. The internal channel 40 is configured for a press-fit engagement with the proximal end of a prepared femoral head. This arrangement serves to prevent the prepared femoral head from bursting or splitting if the patient fully loads the hip joint before bone in-growth into the implant 10 has occurred.

In addition, the porous lattice 33 extends from the planar stop surface 32 to approximately 70% of the distance down the inner surface 42 of the annular skirt 38 so that the internal channel 40 is substantially surrounded by a porous surface for bone in-growth.

The femoral implant 10 of the present embodiment is manufactured from cobalt chrome although other suitable metallic material may be employed.

The formation of the central hollow portion 36 is achieved in this particular embodiment by casting a first part 44 comprising the stem 12 and including the planer stop surface 32 (which is provided on a radial flange 46 at the base 20 of the stem 12) and the annular skirt 38 of the femoral head 14 (which depends in a distal direction from the outer circumference of the flange 46), and a second part 48 comprising the remainder of the part-spherical external surface 34 of the femoral head 14. In this case, both the first and second parts 44, 48 have a cavity therein. The first and second parts 44, 48 are then welded together at interface 50 such that the remainder of the external surface 34 of the femoral head 14 extends in a proximal direction from the outer circumference of the flange 46.

The femoral implant 10 may be employed in situations where the femoral head 14 is arranged to articulate against a patient's normal acetabular cartilage or a prosthetic acetabular cup.

Where a prosthetic acetabular cup is used, the cup itself may be manufactured from cobalt chrome, ceramic or polyethylene material.

Figure 2:
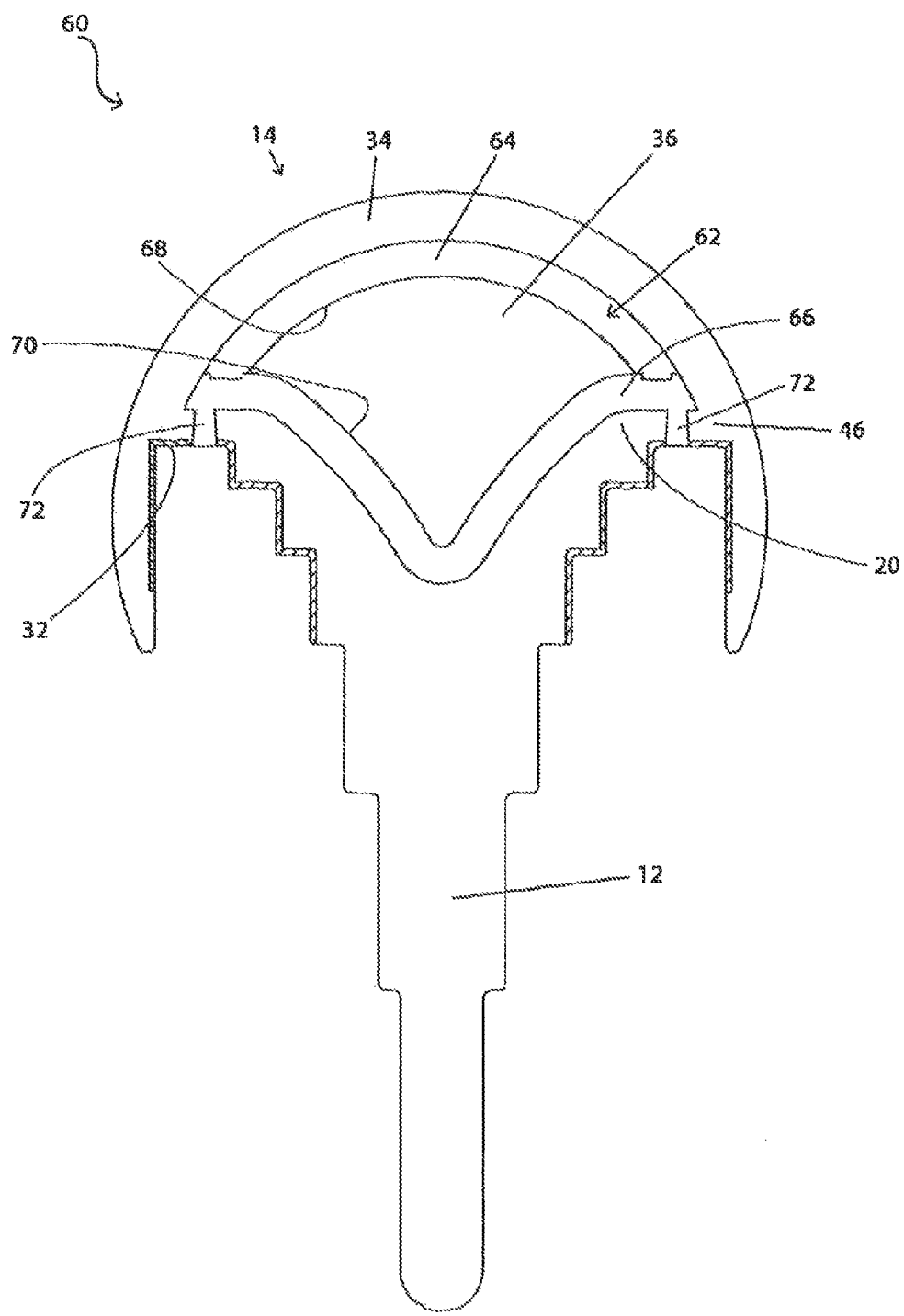
FIG. 2 shows a central cross-sectional view through a femoral implant according to a second embodiment of the present invention, similar to that shown in FIG. 1 but comprising a discrete hollow internal component.

FIG. 2 shows a central cross-sectional view through a femoral implant 60 according to a second embodiment of the present invention. The femoral implant 60 is similar to that shown in FIG. 1 and so like reference numerals will be used where appropriate. However, unlike in FIG. 1, the femoral implant 60 includes a discrete hollow internal component 62.

The hollow component 62 is formed by welding together a first component 64 and a second component 66. The first and second components 64, 66 are each formed from a titanium alloy and have a cavity therein. In practice, the first component 64 is configured to mate with an inner concave surface of the part-spherical external surface 34 of the femoral head 14 and the second component 66 is configured to mate with the surface defining the cavity in the stem 12. The interior surfaces of the hollow component 62 are configured to correspond to the shapes of the external mating surfaces of the hollow component 62 such that the resulting hollow portion 36, is of substantially the same shape as that shown in FIG. 1. More specifically, the hollow portion 36 is bounded by an upper concave part-spherical surface 68 and a lower downwardly tapering curved surface 70 which forms a generally conical portion of the cavity.

Four frusto-conical legs 72 are provided on the second component 66 to position the hollow component 62 within a mould during the casting of the remainder of the femoral implant 10. The legs 72 are evenly disposed around the periphery of the second component 66 and are configured to project through the flange 46 at the base 20 of the stem 12, in a direction substantially parallel to the longitudinal axis of the stem 12. Thus, the legs 72 are initially configured to project into the ceramic slurry of the mould in the region configured to form the internal channel 40.

Once the mould has been hardened, the remainder of the implant is cast in the mould from cobalt chrome. The mould is then removed and the projecting portions of each leg 72 are cut and filed until they are made flush with the surrounding surface of the implant (i.e. the adjacent portions of the planar stop surface 32).

Figure 3:
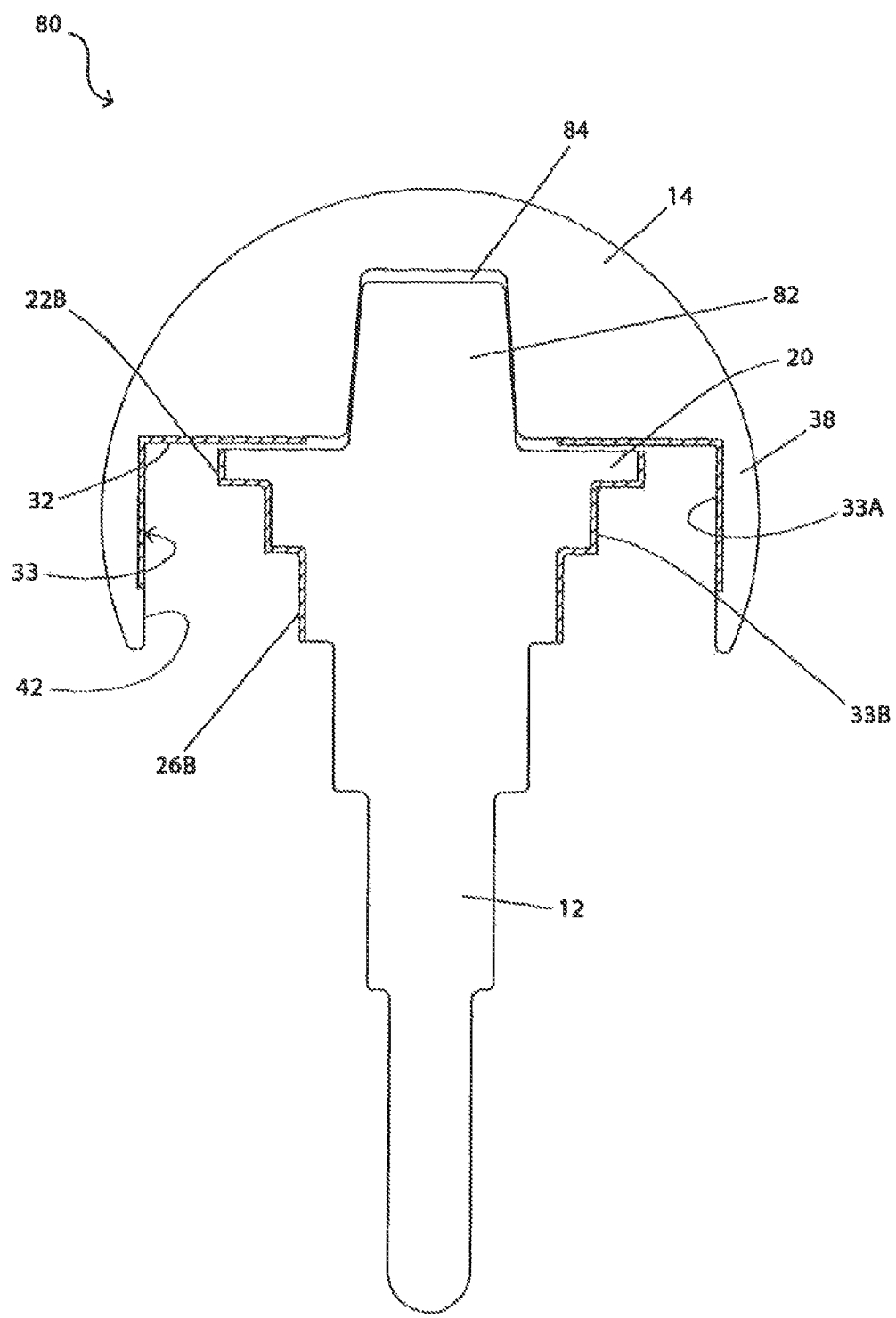
FIG. 3 shows a central cross-sectional view through a femoral implant according to a third embodiment of the present invention, wherein the femoral stem is separable from the femoral head.

FIG. 3 shows a central cross-sectional view through a femoral implant 80 according to a third embodiment of the present invention. The femoral implant 80 is, again, similar to that shown in FIG. 1 and so like reference numerals will be used where appropriate. However, in this case, the femoral stem 12 is separable from the femoral head 14. Accordingly, the stem 12 includes a central frusto-conical spigot 82 extending from the proximal end of the base 20, which is configured to be received in a complementary shaped cavity 84 provided in the internal portion of the femoral head 14, prior to insertion of the implant 80 into a patient. The spigot 82 is conveniently configured for a tight frictional fit within the cavity 84.

It will be seen from FIG. 3 that, in this embodiment, the spigot 82 and cavity 84 occupy the centre of the femoral head 14 and so no internal hollow portions are specifically provided to reduce the weight of the implant 80. It will also be noted that the planar stop surface 32 is provided by a planar internal surface of the femoral head 14 and that the porous lattice 33 is provided in two portions—a first portion 33A being provided on the inner surface 42 of the annular skirt 38 and along the planar internal surface of the femoral head 14 and a second portion 33B being provided on the proximal surface of the stem 12 from the first cylindrical side surface 22B to the third cylindrical side surface 26B.

Figure 4:
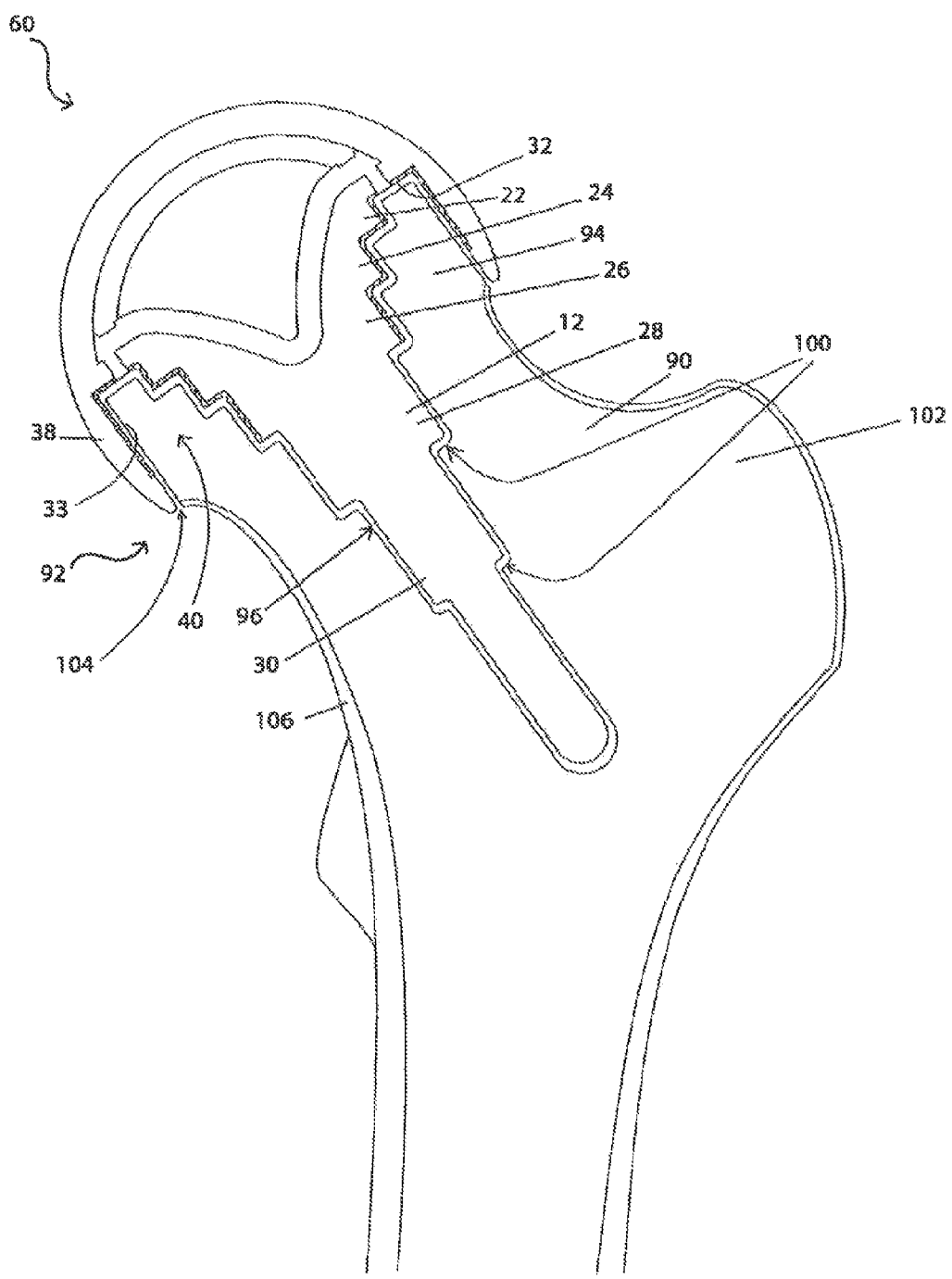
FIG. 4 shows a central cross-sectional view of the femoral component of FIG. 2, when implanted on a resected femur.

FIG. 4 shows a central cross-sectional view of the femoral component 60 of FIG. 2, when implanted on a resected femur 90. However, it will be understood that other embodiments of the present invention could similarly have been shown as implanted on the femur 90, including those illustrated in FIGS. 1 and 3. Accordingly, it will be understood that, in use, the proximal end 92 of a patient's femur 90 is preferably resected towards the distal end of the femoral head 94 and a cavity 96 suitable for receiving the stem 12 is produced through the femur 90 from the resected head 94 by machining, for example milling. A plurality of discrete ledges 100 are formed in the cavity wall, in the soft cancellous bone 102 of the femur 90, for mating with the corresponding steps 22, 24, 26, 28, 30 provided on the stem 12 of the femoral component 60. The femoral implant 60 is then fitted into the cavity 96 until the top of the resected femoral head 94 abuts the planar stop surface 32. In this position, the top of the resected femoral head 94 is received within the internal channel 40, in a press-fit engagement with the skirt 38, and this serves to prevent the prepared femoral head 94 from bursting or splitting if the patient fully loads the hip joint before bone in-growth into the porous lattice 33 has occurred. It will be noted that, although, for reasons of clarity, a gap 104 can be seen between the femur 90 and the femoral component 60 as drawn in FIG. 4, no such gap 104 will be provided in practice as the femur 90 and femoral component 60 will be configured for a precise appositional fit.

It is also clear from FIG. 4, that the stem 12 of the femoral component 60 is spaced, all along its length, from the edges of the femur 90, where hard cortical bone 106 is present and this further helps to reduce the likelihood of stress-shielding.

It will be understood that embodiments of the present invention variously provide for an improved femoral implant 10 which overcomes many of the problems encountered in relation to traditional hip replacement and hip resurfacing techniques. In particular, aspects of the present invention provide an improved fixing of the implant in the femur, improved alignment of the stem and a reduced risk of stress-shielding.

It will be appreciated by persons skilled in the art that various modifications may be made to the above embodiments without departing from the scope of the present invention.

The invention claimed is:

1. A femoral implant comprising:
    a distal end and a proximal end;
    a substantially straight stem provided at the distal end of the implant, the stem comprising a body of generally tapering form extending in a distal direction from a proximal base to a rounded distal tip for insertion into a femur; and
    a femoral head provided at the proximal end of the implant and extending from the base of the stem;
    wherein the body of the stem includes a plurality of discrete steps located between said tip and said base, wherein the steps are concentrated more towards the base of the stem than towards the tip, wherein the steps are distributed along the body such that the distance between each adjacent step gradually decreases towards the base and the steps have stop surfaces with widths that gradually increase towards the base,
    wherein the stop surface of one or more of the steps is a planar distal stop surface extending substantially radially outwardly from the longitudinal axis of the stem,
    wherein one or more of the steps include a substantially cylindrical side surface extending generally parallel to the longitudinal axis of the stem, and
    wherein the steps are configured such that at least the most distal step will have a press-fit engagement into the prepared bone of the femur, and at least the most proximal step will have a line-to-line fit engagement into the prepared bone of the femur.

2. The femoral implant according to claim 1 wherein the steps have stop surfaces each with a width of no less than 2 mm so as to provide an adequate surface area for the transfer of load to the femur.

3. The femoral implant according to claim 1 wherein between the tip and the most distal step, the stem has a width no greater than one fifth of the width of the base.

4. The femoral implant according to claim 1 wherein the surface of the stem from the tip to the most distal step is non-porous.

5. The femoral implant according to claim 1 wherein one or more portions of the stem comprise a porous surface.

6. The femoral implant according to claim 1 wherein the femoral head comprises a part-spherical external surface configured to be received within a corresponding acetabular cup.

7. The femoral implant according to claim 6 wherein a free periphery of the part-spherical surface forms an annular skirt extending around the base of the stem thereby creating an internal channel between the annular skirt and a proximal region of the stem.

8. The femoral implant according to claim 1 wherein the femoral head comprises a central portion which is substantially hollow.

9. The femoral implant according to claim 1 wherein the femoral head is separable from the stem.

10. The femoral implant according to claim 1, wherein the body of the stem includes 3 to 10 steps.

11. The femoral implant according to claim 1, wherein the most distal step from the base of the stem is disposed approximately halfway between the tip and the base.

* * * * *